(12) United States Patent
Lindner et al.

(10) Patent No.: US 7,474,416 B2
(45) Date of Patent: Jan. 6, 2009

(54) SYSTEM AND METHOD FOR MEASURING AN OBJECT AND MONITORING THE SURFACE OF AN OBJECT

(75) Inventors: Björn Lindner, Aachen (DE); Jüergen Phillips, Aachen (DE); René Beaujean, Aachen (DE)

(73) Assignee: Pixargus GmbH, Aachen (DE)

( * ) Notice: Subject to any disclaimer, the term of this patent is extended or adjusted under 35 U.S.C. 154(b) by 264 days.

(21) Appl. No.: 11/256,438

(22) Filed: Oct. 21, 2005

(65) Prior Publication Data
US 2006/0119864 A1 Jun. 8, 2006

(30) Foreign Application Priority Data
Oct. 21, 2004 (DE) .................. 10 2004 052 508

(51) Int. Cl.
*G01B 11/24* (2006.01)
(52) U.S. Cl. .................. 356/606; 356/601; 356/623; 250/201.1; 250/559.06
(58) Field of Classification Search .................. 356/601, 356/606–616, 623; 702/156–170; 250/201.1, 250/559.06–559.08
See application file for complete search history.

(56) References Cited

U.S. PATENT DOCUMENTS

| | | | |
|---|---|---|---|
| 5,880,459 A * | 3/1999 | Pryor et al. | 250/559.08 |
| 5,900,925 A * | 5/1999 | Navarro | 352/243 |
| 6,064,759 A * | 5/2000 | Buckley et al. | 356/603 |
| 7,245,386 B2 * | 7/2007 | Philipps et al. | 356/602 |
| 2004/0246473 A1 * | 12/2004 | Hermary et al. | 356/237.1 |

FOREIGN PATENT DOCUMENTS

| | | |
|---|---|---|
| DE | 689 02 329 T2 | 12/1992 |
| DE | 19739250 A1 | 3/1998 |
| DE | 29910132 U1 | 10/1999 |
| DE | 10328537 A1 | 10/2002 |
| DE | 10120430 A1 | 12/2003 |

* cited by examiner

*Primary Examiner*—L. G Lauchman
*Assistant Examiner*—Iyabo S Alli
(74) *Attorney, Agent, or Firm*—Lathrop & Gage LC

(57) ABSTRACT

A system for measuring an object and for monitoring the surface of the object. The system comprises at least a first subsystem for determining one or more dimensions of the object and a position of the object within the first subsystem, and at least a second subsystem for determining a surface structure of the object. Further, the system comprises a control unit generating control signals (iii) for operation of the second subsystem as a function of data (i) of the first subsystem with respect to a position of the object in the first subsystem and/or the dimension of the object, and of data (ii) of the second subsystem with respect to a position of the camera device in the second subsystem.

36 Claims, 11 Drawing Sheets

SYSTEM AND METHOD FOR MEASURING AN OBJECT AND MONITORING THE SURFACE OF AN OBJECT

RELATED APPLICATIONS

This applications claims priority under 35 U.S.C. § 119 to German patent application DE 10 2004 052 508, filed on Oct. 21, 2004 and incorporated herein by reference.

FIELD OF THE INVENTION

The invention relates to a system and a method for measuring and monitoring a surface of an object. The invention is suitable in particular for the quality control of an object with regard to tolerances and the finish of its surface.

BACKGROUND

The prior art is familiar with certain techniques for inspecting the quality of endless profiles by contactless means. For reliable quality inspection, in particular of continuous profiles, analysis by means of electronic digital image processing has been recently established. Irradiating the surface of the profile by means of a suitable light source and detecting the reflected radiation by an electronic camera device with subsequent electronic image processing provides feedback on the dimensioning and tolerances of an object and on the finish of its surface.

U.S. Pat. No. 6,064,759 discloses the measuring of an object, a light source for structured light, which is arranged obliquely at an angle to the surface of the object, and a recording device arranged perpendicularly to the surface of the object being used. The light source for structured light is a laser. The evaluation of the image points recorded from the object is based on the known methods of digital image processing.

DE 103 28 537 A1 discloses an apparatus and a method for measuring the dimension of an object. In this case, radiation is directed onto the object past a light blocking element, so that a so-called sharp light edge is formed on the surface of the object. A suitable sensor device captures the radiation reflected by the sharp light edge and converts it into image data, with which an image evaluation is subsequently carried out for determining the dimensions of the object.

DE 101 20 430 A1 shows an apparatus for the automatic surface inspection of profiles with electronic camera devices. A continuous profile is passed through a so-called light ring and thereby irradiated with light along its circumference by corresponding light sources which are arranged along the light ring. Electronic camera devices are provided adjacent the light ring, in order to capture light which is reflected by the surface of the profile, in order subsequently to carry out an evaluation of the image points for a surface inspection. However, this apparatus has the disadvantage that, to achieve reliable measuring results, an exact position of the camera devices relative to the profile to be measured must be known, which requires complex setting of the apparatus or complex calibration.

It is an aim of the invention to simplify surface inspection of an object, in particular by means of digital image processing, with regard to equipment setting.

SUMMARY OF THE INVENTION

According to the invention, this aim is achieved by a system with the features of claim 1 and by a method with the features of claim 22. Further embodiments of the invention are defined in of the dependent claims.

According to the invention, the system is suitable for measuring an object and comprises at least a first subsystem and at least a second subsystem. With the first subsystem, a dimension of the object and a position of the object within the first subsystem are determined, and with the second subsystem a surface structure of the object is determined. Both subsystems are expediently based on the principle of digital image processing and may for this purpose respectively comprise an electronic camera device and a suitable light source. According to the invention, the system further comprises a control unit, which generates control signals for operating the second subsystem as a function of data of the first subsystem with respect to a position of the object in the first subsystem and/or the dimension of the object, and as a function of data of the second subsystem with respect to the position of the second camera device in the second subsystem.

According to the invention, the control unit may be an electronic component which generates said control signals for operating the second subsystem. Alternatively, the control unit may also be a program routine. Such a program routine may be executed on any suitable computer, or else be suitably implemented in the first subsystem and/or in the second subsystem. It goes without saying that the control signals that are generated do not necessarily have to be electrical signals.

According to the invention, if the first subsystem comprises an electronic camera device as a recording device, the evaluation of measuring data of the object may be based on the principle of triangulation. Alternatively, instead of an electronic camera device, the first subsystem may also have as a recording device a so-called photo line detector, which in the same way ensures recording of image points of the surface of the object. The same applies analogue for a photo line detector, which is used in a light blocking technique. Herein the object is placed within the radiation field between a light emitter and a light source, respectively, and the photo line detector. According to the invention the photo line detector is of a sensor type detecting at least one line or a plurality of lines such that an information about the width and/or the position of the object inside the first subsystem is received. The at least one line of the photo line detector may comprise photocells that are read out after the irradiation with light.

According to the invention an important feature of the system and the method is that the information or the data that are obtained by the first subsystem on the position and the type of object to be measured within the first subsystem are converted in a suitable control unit into control signals for operating the second subsystem. The control signals that are generated are likewise a function of the data of the second subsystem with respect to the position of the camera device in the second subsystem. In other words, the operation of the second subsystem is based on the data of the first subsystem dependent on the camera position in the second subsystem.

According to a further embodiment, the position of the camera device in the second subsystem may be predetermined before the system is put into operation, i.e. be known in advance. In addition, the second subsystem may be provided with a sensor device, which detects the position of the camera device provided in it and correspondingly sends this information on to the control unit. In either case, it is ensured that, in conjunction with the signals of the first subsystem, the control unit receives information on a distance of the camera device of the second subsystem and on its angular position relative to the object to be measured, which is of great importance for an exact evaluation of the measurement in the digital image processing.

According to a further embodiment, the respective electronic camera devices of the first and second subsystems may be combined in a single electronic camera device. Such a camera device may be formed in particular by a CMOS camera and can be switched over for operation of the first subsystem or the second subsystem. Switching over of the common camera device expediently takes place by suitable electronic signals. In the case of operation of the first subsystem, this electronic camera device is switched to an area mode and, in the case of operation of the second subsystem, it is switched to a line mode. In accordance with switching over of this camera device, the light sources of the first or second subsystem are also switched over.

According to a further embodiment, the common camera device of the two subsystems may be operated in a constant mode, for example an area mode, desired image cutouts being selected in assignment to a respective subsystem and subsequently evaluated. As a result, with respect to the first subsystem, processing of image data from border regions that are not relevant can be avoided. With respect to the second subsystem, in said constant mode of the common camera device, for example the area mode, an evaluation can be based on a single image line or individual image lines.

According to a further embodiment, the recording device of the second subsystem and the camera device of the second subsystem may be arranged in a common housing such that their respective recording regions are adjacent each other. The common housing reduces the production costs and simplifies assembly and, if required, adjustment of the system for servicing purposes and the like. According to the invention, a pointing element may be attached to the camera device of the second subsystem. This pointing element can be detected in dependence on a position of the recording device of the first subsystem. In the simplest case, the pointing element may be a rod, for example made of metal, which protrudes into a recording region of the recording device of the first subsystem. As an alternative to this, the pointing element may be formed by optical means, which project a point or the like into the recording region of the recording device of the first subsystem. Correspondingly, information on the position of the second camera device in the second subsystem is obtained, since the relative position of the second subsystem in relation to the first subsystem is known.

According to a further embodiment, the camera device may be fixedly arranged in the second subsystem. An adjustability of the camera device in conjunction with motor drives, moved cables, sensors or the like is then not necessary. As a result, the system comprises a construction being inexpensive, since it is simple and robust. Even in the case of a fixed camera device of the second subsystem, an adaptation to dimensions of an object of various sizes can be performed, in that a parameter adaptation with respect to the measured/metered values of the surface structure of the object is executed in response to the data of the first subsystem with respect to the position of the object in the first subsystem and/or the determined dimension of the object. This may advantageously be executed, for example, by an angle transformation with respect to the metered values of the surface structure of the object, on the basis of which the area recorded at an angle by the second camera device is transformed into a perpendicular plane. This results in an imaging correction of the surface structure. This enables a correction of the imaging of defects on the surface.

According to a further embodiment, the position of the camera device in the second subsystem relative to the object can be adjusted in response to the control signals of the control unit. The adjustment of the second camera device may take place profile-radially, profile-tangentially or profile-axially with respect to the object to be measured. Furthermore, an angle of a recording axis of the camera device may be varied with respect to the perpendicular to the surface of the object. This provides a fourfold spatial adjusting capability for the camera device in the second subsystem. A respectively adapted distance of the camera device in respect of bodies of different sizes in this case advantageously ensures an exact evaluation of image points of the surface of the object. The adjustment of the camera device may either be performed manually by an operator, a setpoint value for a desired camera position being indicated by the control signals of the control device or, alternatively, an adjustment of the camera device may take place automatically, for example by motor, by means of the control signals of the control device.

According to a further embodiment, the electronic camera device of the second subsystem may be inclined at an angle to the perpendicular of the surface of the object. In particular for the case where this angle is smaller than the angle of reflection with respect to the angle of incidence of the light which is radiated onto the surface of the object, the so-called dark field method may be used for the surface inspection. This method offers excellent compensation for otherwise locally dominant lightening effects in the case of porous material surfaces. The surface of the object may also be additionally scanned by other suitable methods.

According to a further embodiment, the control unit may be connected to a first database, in which data of dimensions for predetermined object profiles are stored. In the case that a dimension and/or the dimensions of the object are determined, the first subsystem can consequently recognize/identify a specific object, the dimensions of which are stored in the first database. Correspondingly, the control signals of the control unit are generated dependent on these data, i.e. as a function of the data of the first database, in order e.g. to adapt the position of the second camera device in the second subsystem to the dimension of the object. In the case of a fixedly arranged second camera device of the second subsystem, or where an adjustment of the cameras is not performed in the case of a movable configuration, a distance between the object and the second camera device is known on account of the data of the first database, which can be made the basis of a parameter matching, as explained above.

According to a further embodiment, the control device may be connected to a second database, in which data of quality attributes for predetermined object profiles may be stored. Dependent on the data of the second database, the second subsystem is consequently provided with the information as to which surface regions of the object are to be inspected with which quality criteria. The second database therefore contains information on which region of the surface of the object must satisfy which quality attributes, which correspondingly influences the control signals of the control unit and ultimately the evaluation of the digital image processing of the metered values of the second subsystem.

According to a further embodiment, a range of metered values of the second subsystem can be manually fixed by an operator with respect to a surface of an object. By means of known input interfaces, such as a touch screen for example, the operator can precisely select the region of the surface of the object of which the surface structure is to be determined or investigated. The input interface can display to the operator, for example, a cross-sectional view of the object, within which the operator can select the region of the surface of the object that is to be analyzed. In addition or as an alternative to this, the range of metered values with respect to the surface of the object can be fixed as a function of the data stored in the first or second database.

According to a further embodiment, a laser device may be the light source of the first or second subsystem. Alternatively, the light source may also comprise an LED array, the light-emitting diodes emitting radiation towards the object past a light blocking element onto the surface of the object, in order to form a light edge on the object. The use of light-emitting diodes (LEDs) has the significant advantage over the use of a laser of lower production costs and entirely uncritical handling of the LEDs with respect to compliance with health and safety regulations.

According to a further embodiment, CCD cameras or CMOS cameras, either in the form of a line camera or else in the form of an area camera, may expediently be used as the electronic camera device for the second subsystem, in particular in connection with a digital image evaluation. The advantage of a line camera over an area camera is a more homogeneous illumination of the surface of the object and the recording of only a single line, which allows greater take-off speeds of continuous profiles through the system. According to the invention, an area camera may be operated in such a way that it is coupled with a stroboscope, which ensures suitable illumination of the surface of the object to be examined with at the same time low use of energy.

According to a further embodiment, the method according to the invention comprises the following steps: determining of a dimension of the object by means of the first subsystem, which comprises at least one recording device and a first light source; determining of a surface structure of the object by means of the second subsystem, which has at least one electronic camera device and a second light source; and generating of control signals for operation of the second subsystem as a function of data of the first subsystem with respect to a position of the object in the first and second subsystems and/or the dimension of the object, and as a function of data of the second subsystem with respect to the position of the camera device in the second subsystem.

According to a further embodiment, the control signals for the operation of the second subsystem may expediently be generated by the control unit referred to above.

According to a further embodiment, the communication of the two subsystems with each other may have the effect of creating a system which offers the user an unattained level of dependability of the inspection. As explained above, the data on the position of the profile in the second subsystem, the type of profile and the position of the camera device in the second subsystem serve as a basis for generating control signals which are formed, for example, by the control device for operation of the second subsystem. The first subsystem may automatically recognize the profile of the object to be measured on the basis from the data stored in the first database. The first subsystem may also detect the rotational position and the position within the overall system. The second system either "knows" its camera positions itself (for example in the case of a fixedly arranged camera device with a predetermined position) or the camera device is provided with a pointing element, which protrudes into the "field of view" of the recording device of the first subsystem, or which in the form of optical means, which project a point or the like into the recording region of the recording device of the first subsystem, can be detected by this recording device. As a result, the first subsystem determines the camera position of the second subsystem and transmits this to the control unit.

According to a further embodiment, the determination of the position of the camera device in the second subsystem is likewise possible by suitable sensor devices. Accordingly, the second subsystem can calculate the profile areas of the object that are visible to it and, if appropriate, carry out various parameter matching operations that are necessary for optimal surface inspection. Parameter matching operations may be construed as an adaptation of parameters. For example, the second subsystem may inform an operator of a point of intersection at which point the second camera device is to be positioned. As an alternative to this, the position of the camera device in the second subsystem remains unchanged, the second subsystem transforming the area observed obliquely at an angle into a perpendicular plane, whereby an imaging correction of surface defects is obtained. This is also meaningful for the case in which the cameras are manually adjusted, since any curved profile surface causes imaging errors for the camera.

According to a further embodiment, in addition to the dimension of the object, the first subsystem may also determine the position of the object inside the first subsystem. Since the alignment of the first subsystem relative to the second subsystem is generally known, the information on the position of the object in the first subsystem at the same time also supplies information on the position of the object in the second subsystem, which is used for the adjustment of the camera device(s) in the second subsystem, as explained above.

According to a further embodiment, the operation of the second subsystem, with which the surface structure of the object is determined, on the basis of the data of the first subsystem and the data with respect to the position of the camera device in the second subsystem is advantageous in that the second subsystem does not necessarily have to be recalibrated for the measurement of bodies of different sizes, since the second subsystem can be set to the new object dimensions. In the case of a fixedly arranged camera device of the second subsystem, a better evaluation of the measuring results of the surface structure is possible, since the positional angle between the second camera device and the object and also the distance between the second camera device and the object can be calculated. Furthermore, the range of metered values of the second subsystem can be automatically fixed on the basis of the data of the first subsystem, for example when a predetermined object profile is detected, without an operator having to set this manually.

According to a further embodiment, the first subsystem may also be divided in two such that in a first part, merely the dimension of the object is determined, while in a second part the position of the object relative to this part is determined. On this basis, the first subsystem is constructed from two part-systems, which however, when combined, supply the same information or data as the one-part first subsystem explained above.

According to a further embodiment, a computer program comprises program coding means to carry out at least part of a step of the method referred to above, in particular at least part of the step in which the control signals are generated as a function of the data of the first database and/or as a function of the second database. This computer program can be executed on a computer or on a corresponding processing unit.

According to a further embodiment, the subsystems may be operated with separate programs. As an alternative to this, the programs may be "fused" or combined with one another in any combination. Furthermore, the systems may be subdivided into any number of further subsystems. For example, the control unit may be separate from a database connection and a parameter adaptation unit. The programs may also run on one computer unit or on any number of computer units in a distributed manner. The input connection may likewise be a submodule or an independent program.

According to a further embodiment, the computer program product comprises program coding means, which are stored on a computer-readable data carrier, in order to carry out the methods described above when the computer program product is executed on a computer or a corresponding processing unit, and in particular the step in which the control signals are generated as a function of the data of the first database and/or as a function of the second database. The program coding means are preferably stored on a computer-readable data carrier. EEPROMs and flash memories, but also CD-ROMs, floppy disks, hard disk drives or the like, may be used as suitable data carriers.

Further advantages and refinements of the invention are provided by the description and the accompanying drawings.

It goes without saying that the features mentioned above and those still to be explained below can be used not only in the respectively specified combination but also in other combinations or on their own without departing from the scope of the present invention.

DETAILED DESCRIPTION TO DRAWINGS

Figure 1:
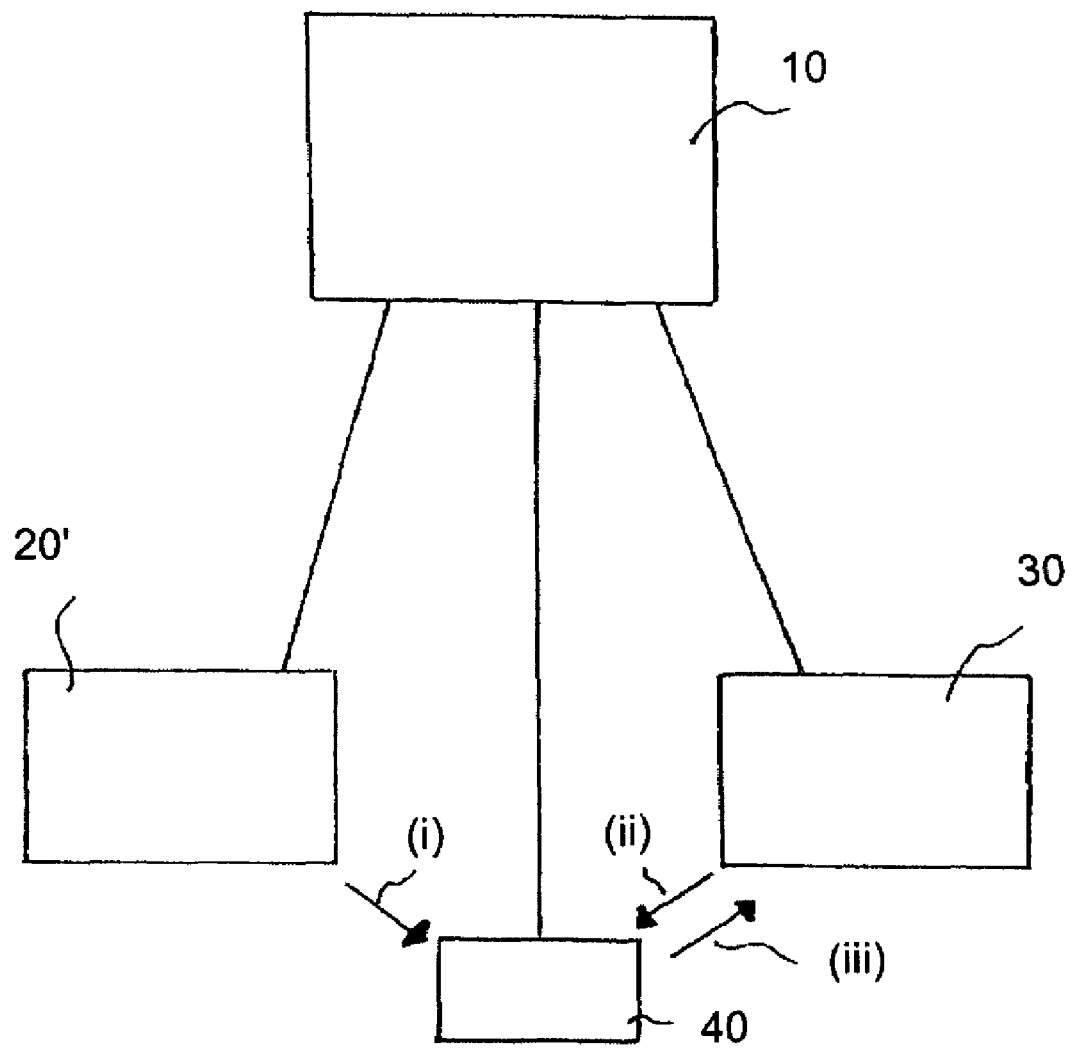
FIG. 1 shows, in principle, a simplified view of a system.

In FIG. 1, a system 10 for measuring an object is symbolically shown in simplified form. The system 10 has at least one first subsystem 20 and at least one second subsystem 30. The system 10 further comprises a control unit 40, which generates control signals for operation of the second subsystem 30. As explained above, the control unit 40 may be a suitable electronic component. Alternatively, the control unit may also be construed as a program routine which can be executed on any computer, or which may be suitably implemented in the first subsystem 20 or the second subsystem 40.

The first subsystem 20 is for determining a dimension of an object. For this purpose, the first subsystem 20 comprises at least a first electronic camera device and a first light source. The first light source irradiates the object from a direction essentially perpendicular to the surface of the object, the first electronic camera device being arranged in such a way that its recording axis forms an angle with the perpendicular to the surface of the object or with an axis along which the object is moved on the first camera device. Such an arrangement of the light source and the electronic camera device is suitable for a digital image processing, it being possible for the dimensions of the object to be determined, for example, by triangulation.

The second subsystem 30 is used in determining a surface structure of the object. For this purpose, the second subsystem 30 comprises at least a second electronic camera device and a second light source. The second light source may be formed as a so-called light ring (cf. FIG. 8), whereby uniform illumination of the object from all sides is ensured. With suitable arrangement of the second electronic camera device relative to the second light source, the surface of the object can be analyzed by the known principle of the dark field technique.

In accordance with the invention, an important feature of the system 10 is provided by a data communication between the first subsystem 20 and the second subsystem 30, as explained in detail below.

For determining its dimension, an object is passed through the first subsystem. In this case, both the dimension of the object and its position within the first subsystem 20 are determined. The first subsystem 20 is connected to the control unit 40, the data of the first subsystem 20 with respect to the position and dimensions of the object being transmitted to the control unit 40. In FIG. 1, this is shown by an arrow (i). The control unit 40 is also connected to the second subsystem 30. The arrow (ii) indicates that the control unit 40 receives from the second subsystem 30 information on the position of the second camera device provided in the second subsystem 30. On the basis of the data (i) and (ii) of the first and second subsystems 20, 30, the control unit generates control signals, which are output to the second subsystem 30 (arrow (iii) in FIG. 1). Consequently, the second subsystem is operated dependent on the data (i) of the first subsystem with respect to a position of the object within the first subsystem and the data (ii) of the second subsystem with respect to the position of its camera device.

For an exact and reliable inspection of the surface of an object by means of a digital image processing, it is very important to know both the distance of the second electronic camera device from the object and the angle of the recording region of this camera device in relation to the surface of the object. Only with the knowledge of this information can the image points of the surface of the object be exactly evaluated, in order to obtain information and feedback on the surface structure. By means of the control signals of the control unit, a radial distance of the second camera device relative to the object can be changed manually or by motor means. Furthermore, the second camera device can be turned around the object, so that different areas of the object can be recorded by the second camera device. Similarly, the angle between the object axis and a recording axis of the camera device can be changed. As an alternative to this, in the case of a fixed camera device, a parameter matching is carried out with respect to the measured values of the surface structure of the object, whereby the second subsystem 30 is likewise adapted to different bodies. A parameter matching is based on an appropriate parameter adaptation.

Figure 2:
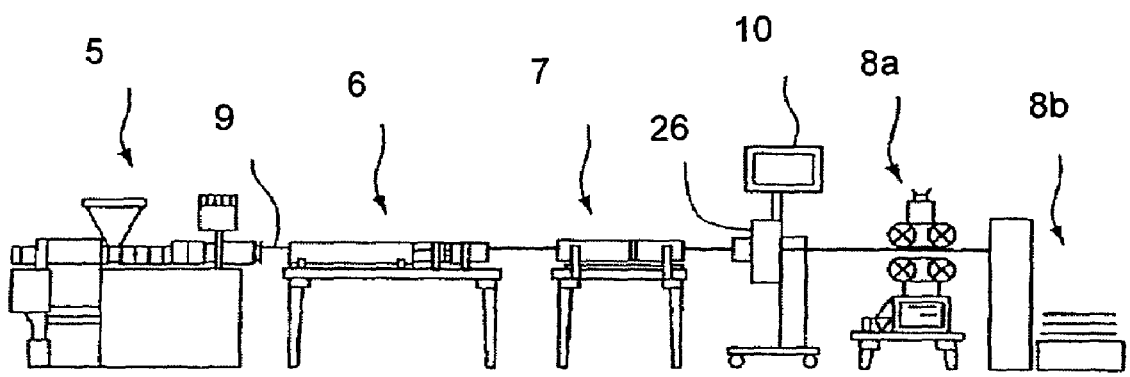
FIG. 2 shows a side view of an extrusion line with the system from FIG. 1.
Figure 3:
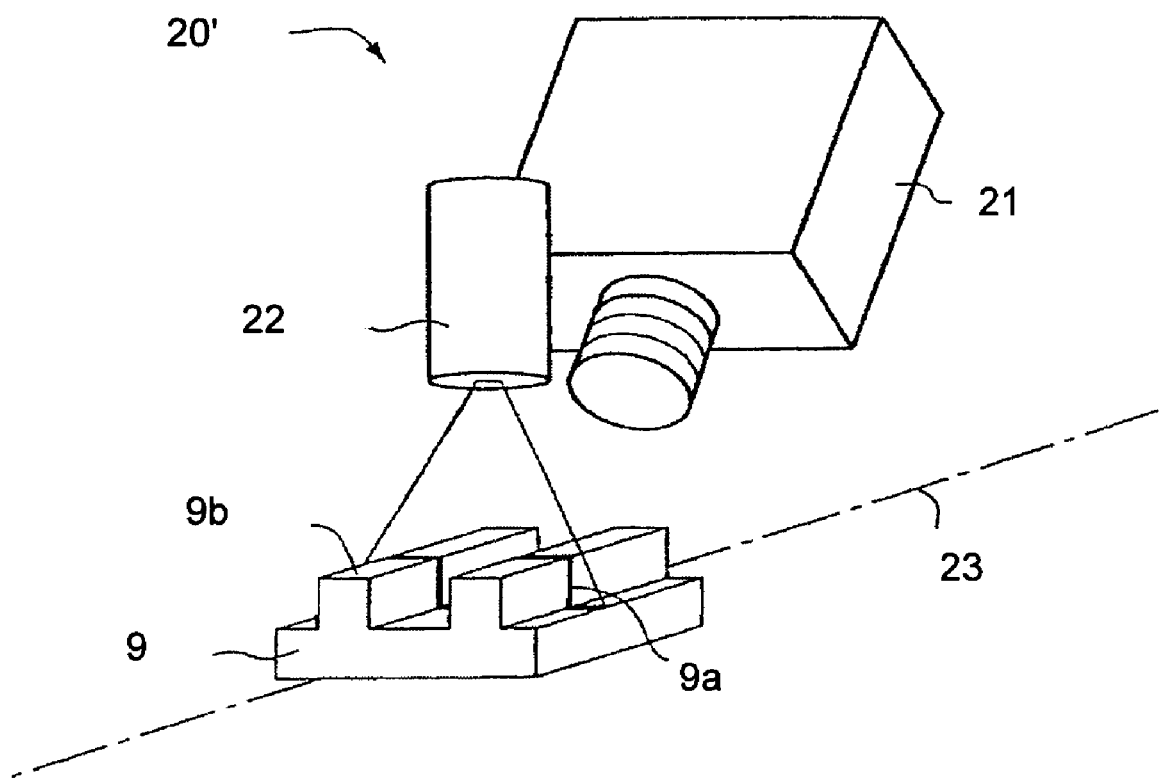
FIG. 3 shows in simplified form an electronic camera is device with a corresponding light source of the first subsystem.

In accordance with the invention, the system 10 may be readily integrated in a continuous production process, as is shown in FIG. 2. A conventional extrusion installation comprises an extruder 5 with a mold, cooling stations 6, 7, a take-off unit 8a and a cutting device 8b. The extruder 5 extrudes an object 9, which then runs through the cooling stations 6, 7 and is finally cut off to the desired length by the cutting device 8b.

In accordance with the invention, the system may be readily integrated in the extrusion installation between the cooling station 7 and the take-off unit 8a. A housing 26 of the system 10 in this case has through-openings, through which the extruded object 9 is taken off by the take-off unit 8a. In accordance with the invention, the first subsystem 20 and the second subsystem 30 may be accommodated in the common housing 26 which ensures a compact and small system. The arrangement of the system 10 as an element of the extrusion installation makes it possible to perform a quality control of the extruded object 9 with respect to tolerances and surface quality directly during production. By suitable interconnection of the system with the cutting device 8b, regions of the object 9 that have defects can also be specifically cut out.

A possible construction and the functional principle of the first subsystem 20 are explained in FIGS. 3 to 6.

For determining the dimension of the object 9 by means of digital image processing, the first subsystem 20 has an electronic camera device 21, the recording region of which is directed at the object. The first subsystem 20 further comprises a first light source 22 in the form of a laser, which is directed at the object 9 and forms a light edge 9a on the surface of the object 9. The first electronic camera device 21 is arranged with its recording axis at an angle to the perpendicular with respect to an axis 23, along which the object 9 is moved. In this way, the image points of the light edge 9a can be evaluated by means of the known method of triangulation, in order as a result to determine the dimensions of the object 9. For measuring the object 9 from different sides, it is advantageous to provide a plurality of the electronic camera devices 21. For example, four camera devices 21 may be arranged along a circular form around the axis 23, in order to ensure a recording region along the circumference of the object 9. It goes without saying that a plurality of first light sources 22 may also be provided in this case, a first light source respectively being assigned to one of the first electronic camera devices 21.

Figure 4:
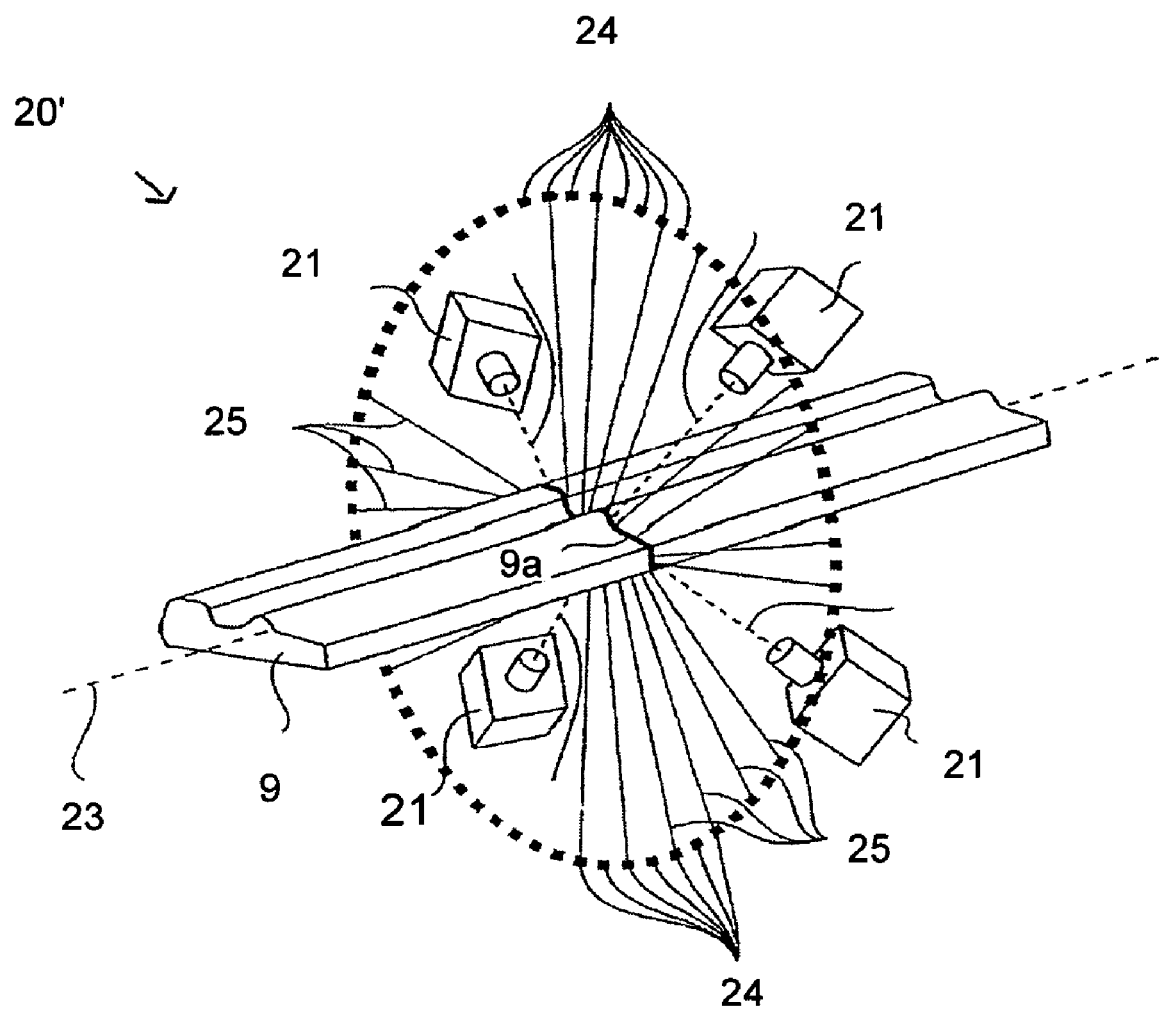
FIG. 4 shows a simplified perspective view of the construction of the first subsystem.
Figure 5:
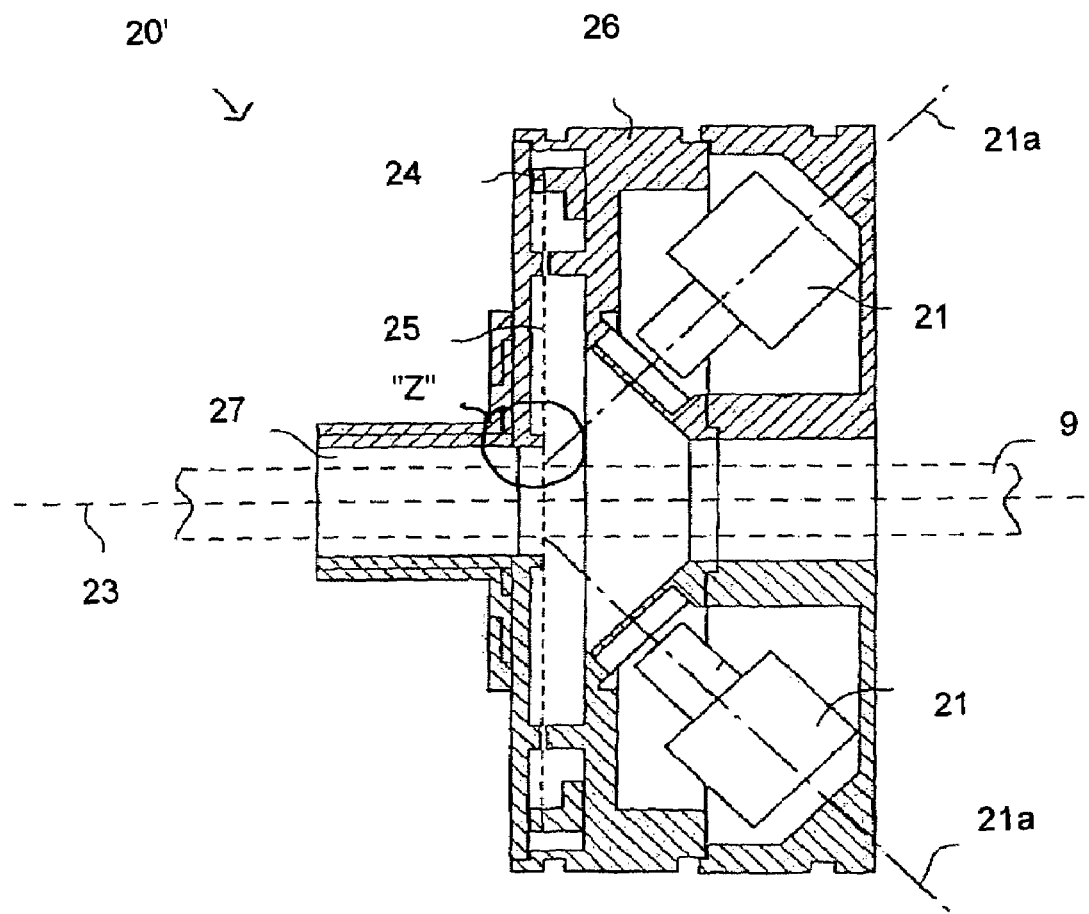
FIG. 5 shows the construction of the first subsystem from FIG. 4 in a lateral cross-sectional view.
Figure 6:
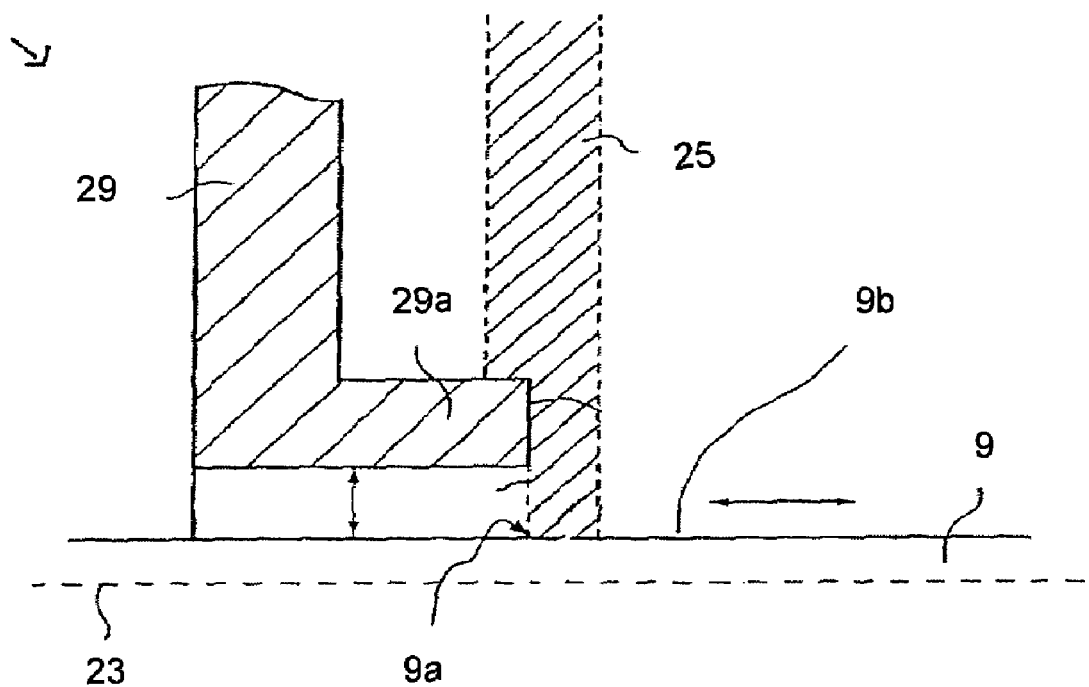
FIG. 6 shows the detail Z from FIG. 5.

An further embodiment of the first subsystem 20' is shown in FIGS. 4 to 6. In the same way as in the case of the embodiment from FIG. 3, four first electronic camera devices 21, which are directed with their recording region toward the object 9, are provided along a circular form around the axis 23. The object 9 is moved past the first electronic camera devices 21 along the axis 23. Different to FIG. 3, the first light source is formed by a plurality of light-emitting diodes (LEDs for short) 24, which are likewise arranged in a circular form around the axis 23. The LEDs 24 respectively emit radiation 25 in the direction of the object 9 past an obscuration device (FIG. 6), so that, in the same way as in the case of the laser, a light edge 9a is formed on the surface of the object 9. In a known way, the dimension of the object 9 can consequently be determined by the first electronic camera devices 21 by means of triangulation. According to FIG. 4, the visible outline of the object 9 is determined on which the subsequent data evaluation is executed.

In FIG. 5, the first subsystem 20' from FIG. 4 is shown in a lateral cross-sectional view. The first electronic camera devices 21 are arranged with their recording axis 21a obliquely at an angle to the perpendicular with respect to the axis 23 in a housing 26 of the first subsystem 20. The housing 26 has a through-opening 27, through which the object 9 can be moved along the axis 23. Furthermore, in the housing 26, the LEDs 24 are arranged in a circular form around the axis 23, the radiation 25 of the LEDs 24 being respectively directed in the direction of the object 9. Formed in the housing 26 in the vicinity of the surface of the object 9 is an obscuration device 28, which blocks out part of the radiation 25 of the LEDs 24, in order to form a so-called sharp light edge 9a on the surface of the object in the same way as a laser. Radiation reflected by the light edge 9a is respectively recorded by the first electronic camera devices 21 and converted into corresponding image points, followed by a digital image processing on the basis of a triangulation, in order to determine the dimension of the object.

FIG. 6 shows the detail "Z" of FIG. 5, in order to illustrate the obscuration device 28. A covering plate 29 of the housing 26 has a projection 29a, which reaches into the path of rays of the radiation 25. In this way, part of the radiation 25 is blocked out, so that the so-called sharp light edge 9a is produced on the surface of the object 9. In accordance with the invention, the term "light edge" is to be understood as a sharp contrast between a region of the surface of the object 9 that is irradiated by the radiation 25 and a region of the surface adjacent to it that is not irradiated. The feature of the so-called light edge is not just based on the wavelength range of visible light. The recording region of the first electronic camera devices 21 (not shown in FIG. 6) is exactly aligned with the light edge 9a, so that a reliable and trouble-free capturing of points of reflection on the light edge 9a by the camera devices 21 is ensured. In FIG. 6, the direction of movement of the object 9 along the axis 23 is indicated by an arrow. When the object 9 is moved along the axis 23, the radiation 25 consequently falls continuously onto a surface 9b of the object 9, so that, as a result, the object 9 can be measured uninterruptedly.

Figure 7:
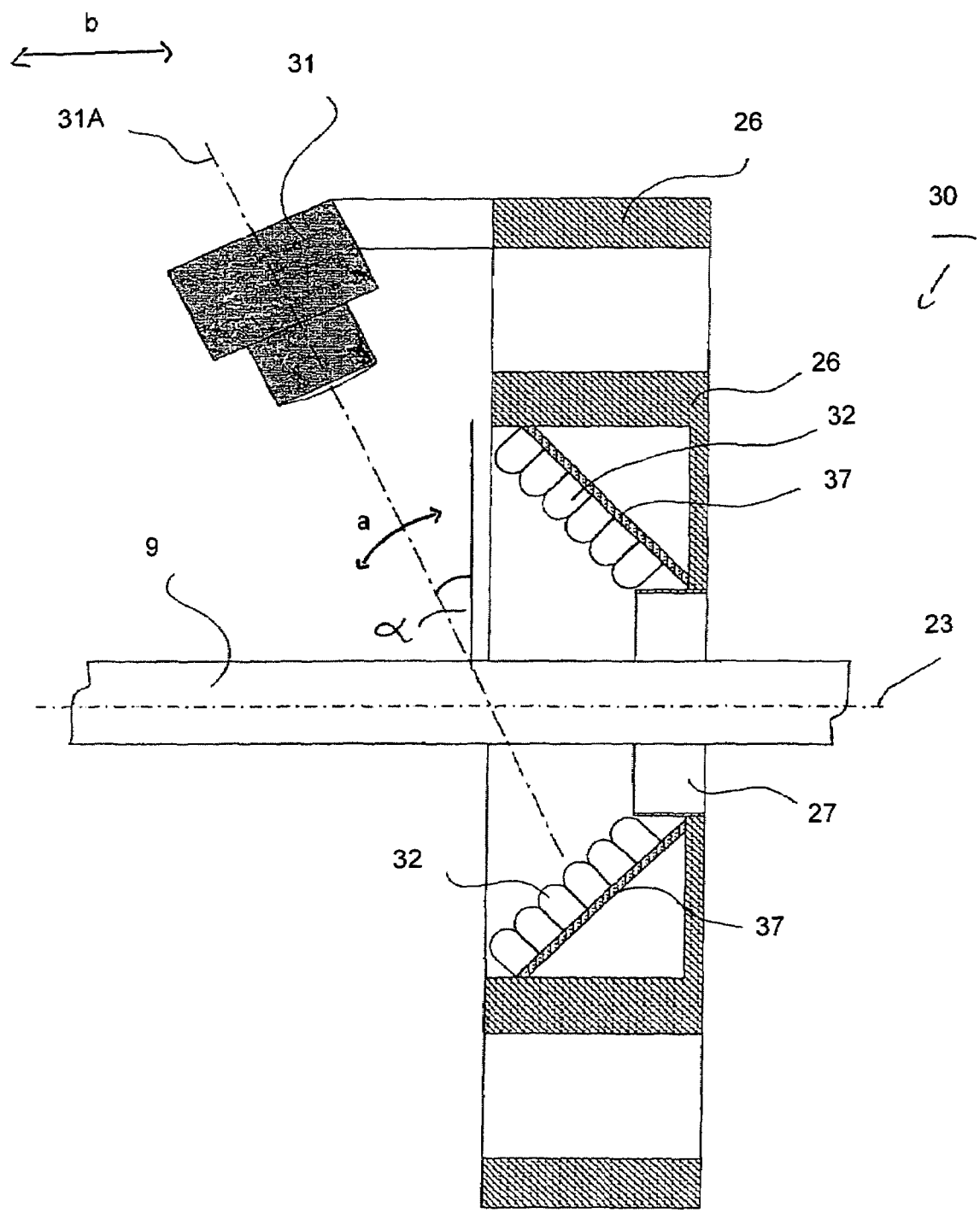
FIG. 7 shows a simplified lateral sectional view of the construction of the second subsystem.
Figure 8:
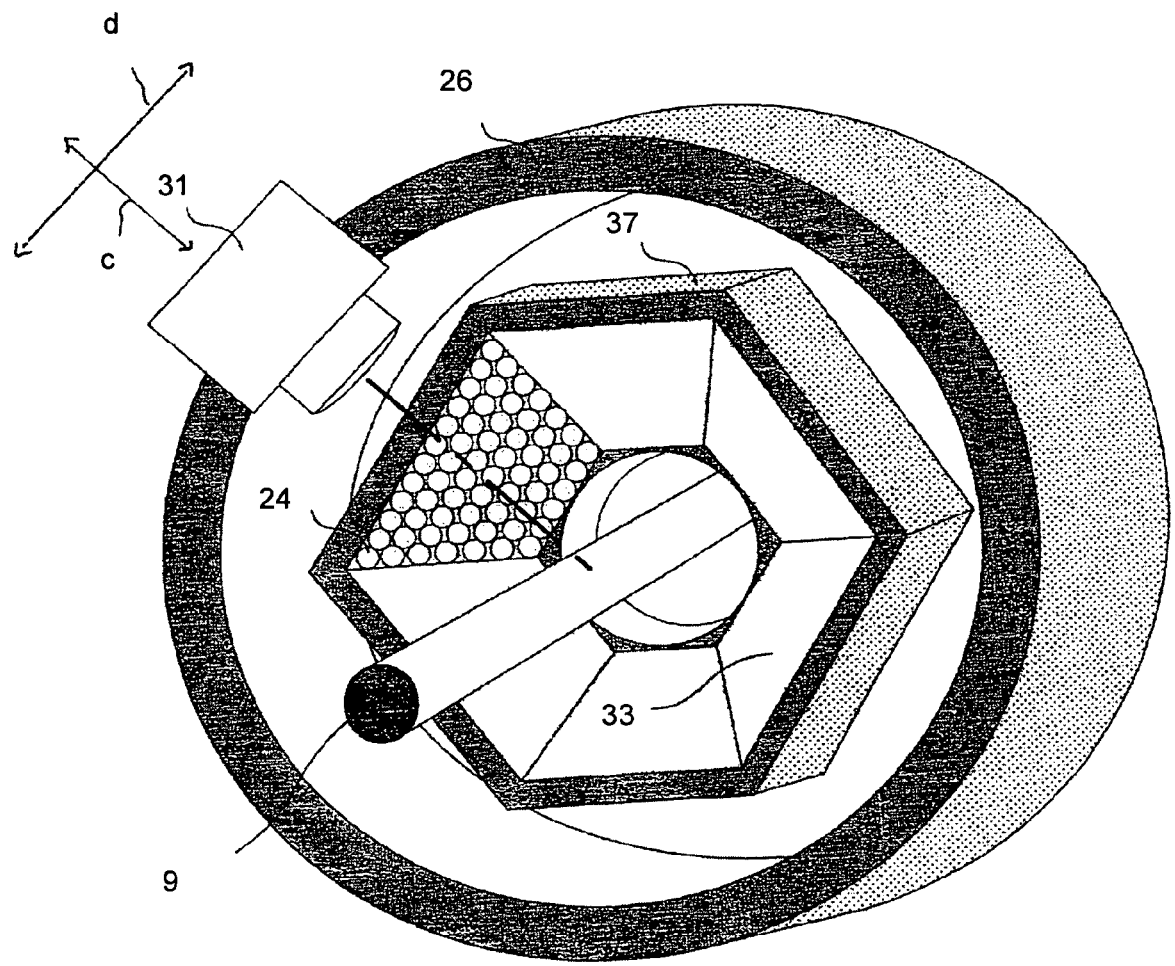
FIG. 8 shows the second subsystem from FIG. 7 in a perspective representation.

In FIGS. 7 and 8, a construction of the second subsystem 30 is shown. A plurality of second electronic camera devices 31 (only one unit is shown in FIG. 7) is arranged in the form of a ring or circle around the axis 23 in the housing 26 of the system 10. The second electronic camera devices 31 are in this case arranged in the housing 26 in such a way that a recording axis 31A of the respective camera devices 31 forms an angle α with a plane which is perpendicular to the axis of movement (23) of the object.

The camera devices 31 are adjustable relative to the axis 23 in such a way that the angle α can be increased or reduced (arrow a in FIG. 7). In addition, the camera devices 31 can also be adjusted profile-axially, i.e. parallel to the axis 23 (arrow b in FIG. 7).

The second subsystem 30 further comprises a second light source 32 in the form of a plurality of light-emitting diodes (LEDs), which are provided in a closely packed form on an annular object 37. An irradiation of the object 9 by the LEDs 32 from all sides is ensured by the object 9 being passed through the annular object 37. The angle α between the recording axis 31A of the second camera device 31 and the alignment of the annular object 37 or the LEDs 32 relative to the axis 23 are in this case suitably chosen and adjustable such that recording of the surface of the object 9 by the electronic camera device 31 can take place on the known principle of the dark field technique or any other advantageously achievable image characteristics.

In FIG. 8, the embodiment from FIG. 7 is represented with an annular object 37 of a hexagonal basic form. The mounting for the LEDs 32 is subdivided into six trapezoidal segments 33, which are in each case inclined by an angle of 45° with respect to the axis 23. A simplified process for producing the diode arrangement is made possible in this way. Other polygonal forms are likewise suitable for the annular object. For the fine adaptation to different diameters of the object 9 to be measured, a profile-axial adjustment of the relative positions of the light ring, i.e. of the LEDs 32, and also the respective electronic camera devices 31 is possible. In this way, a constancy of the illuminating characteristics can be achieved.

The second electronic camera device 31 of the second subsystem 30 can be adjusted manually and/or by electric motor both profile-radially and profile-tangentially in the housing 26. The profile-radial adjustment (arrow c in FIG. 8) allows the distance of the second camera device 31 from the object 9 to be reduced or increased, so that even in the case of bodies of different sizes the distance between the object and the camera device 31 is constant. Furthermore, the profile-tangential adjustment (arrow d in FIG. 8) of the camera device, i.e. turning of the camera device along the circular housing 26, allows different circumferential portions of the object 9 to be measured.

The camera devices 21 of the first subsystem 20 can be adjusted in the same way as the camera devices 31 of the second subsystem 30 in adaptation to bodies of respectively different sizes that are to be measured. In other words, the camera devices of both subsystems can be adjusted not only with respect to the angle of their recording axis in relation to a perpendicular to the axis 23 but also profile-radially, profile-tangentially and profile-axially. This respectively produces four degrees of spatial freedom for the corresponding camera devices.

Figure 9:
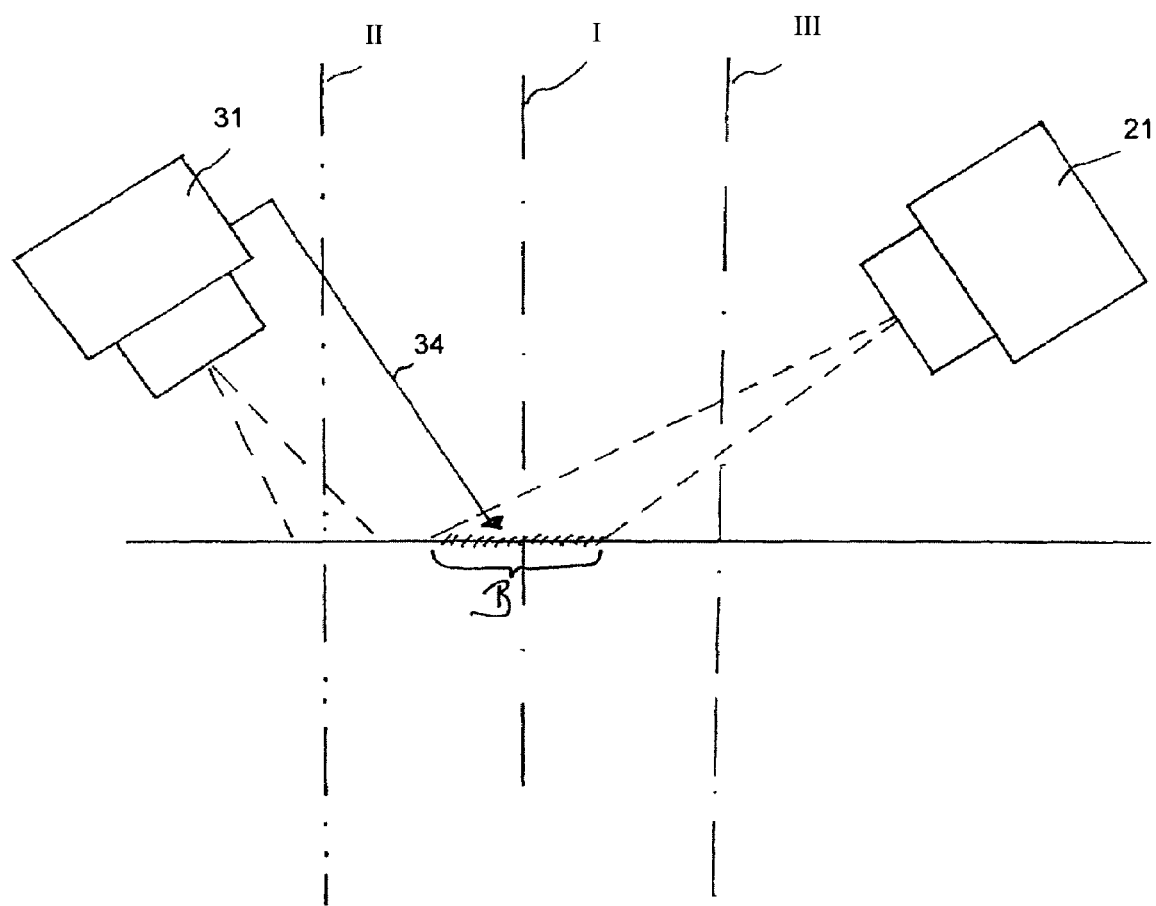
FIG. 9 shows an arrangement of the first and second subsystems relative to each other.

The first camera devices 21 of the first subsystem 20 and the second camera devices 31 of the second subsystem 30 may be both arranged in the housing 26. This advantageously makes the system 10 more compact. The arrangement of the camera devices 21, 31 is chosen such that their respective recording regions are adjacent each other. In FIG. 9, this is indicated by the planes I to III. The recording axes of the camera units of the two subsystems may also be arranged in any spatial directions. The first electronic camera device 21 of the first subsystem 20 comprises a recording region B, in which the plane I lies. The plane I is adjacent the plane II, which lies in the recording region of the second electronic camera device 31 of the second subsystem 30. A pointing element 34 (shown in simplified form) can be mounted to the second electronic camera device 31. The pointing element 34 can protrude into the recording region B of the first camera device 21 in dependence on the position of the second camera device 31. In the simplest case, the pointing element 34 may be a metal rod or the like, which, as explained, protrudes into the recording region B. As an alternative to this, the pointing element may be formed by optical means, which project a point or the like into the recording region B.

If the pointing element 34 or its projection protrudes into the recording region B and is correspondingly detected by the first electronic camera device 21, this allows feedback concerning the position of the second camera device 31 within the second subsystem 30. This applies in the same way to the case in which the second electronic camera device 31 is adjusted in the second subsystem 30 along the circular arrangement, so that the pointer element 34 arrives in the recording region of another electronic camera device 21. In the case of a plurality of second camera devices with corresponding pointer elements, it is possible by suitable coding or the like of the pointer elements or their projections to obtain exact information on the position of the second camera devices in the second subsystem 30 by means of a detection by the first electronic camera devices. The optical coding of a projection of a respective pointing element may be achieved, for example, by a representation of letters, numerals, a varying number of dots or the like.

Figure 10:
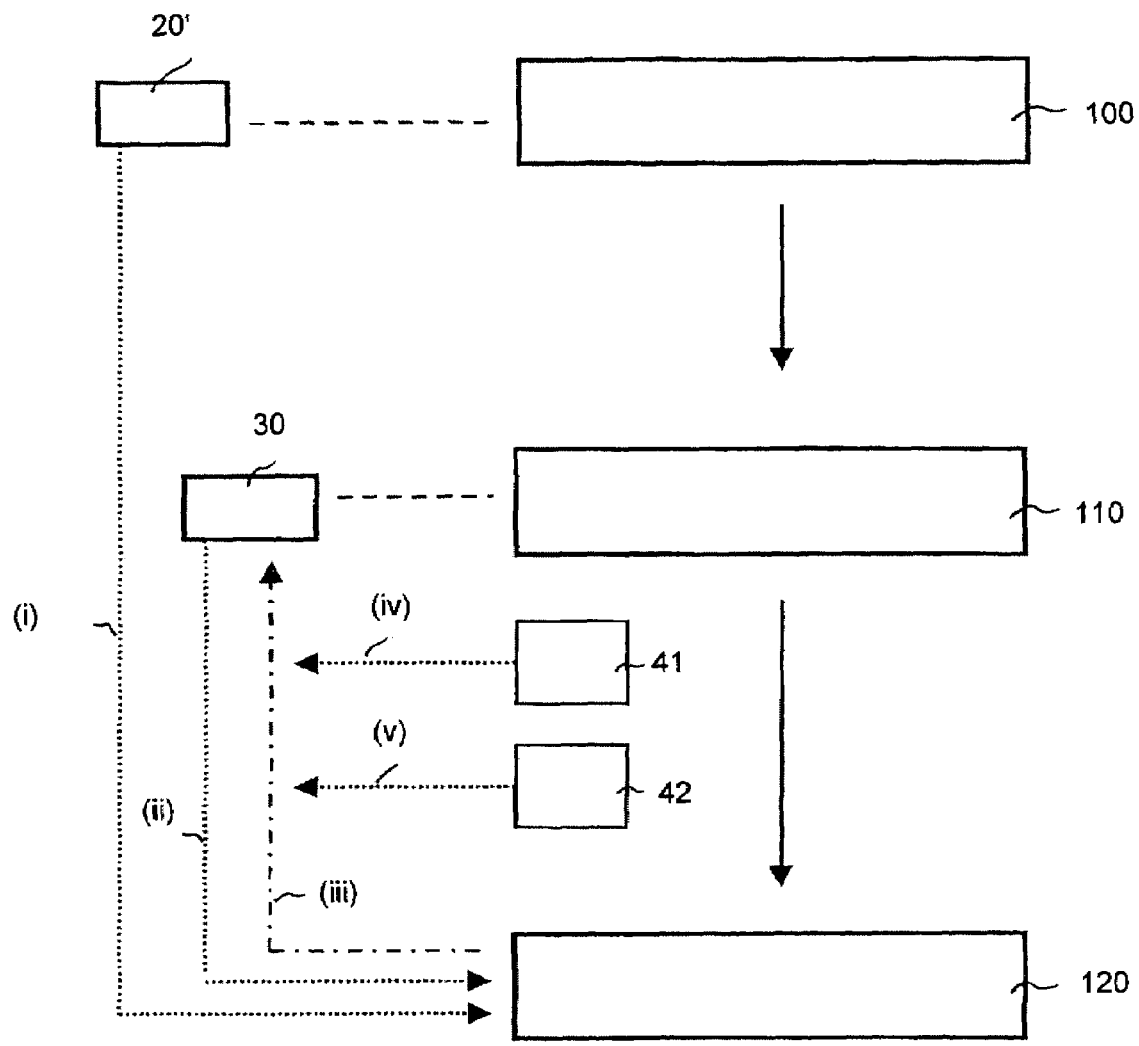
FIG. 10 shows a sequence of method steps.

FIG. 10 illustrates in a flow diagram the sequence of steps of the method. In accordance with the invention, in a step 100, a dimension of the object is determined by means of the first subsystem 20. Furthermore, in a step 110, a surface structure of the object is determined by means of the second subsystem 30. The term surface structure is to be interpreted very broadly in this connection, and covers any change of the surface in the form of drilled holes, a flocking, an imprint or other structures that deviate from an otherwise completely smooth surface of the object. In a next step 120, control signals for operation of the second subsystem are generated. These control signals are a function of data (i) of the first subsystem 20 with respect to a position of the object 9 in the first subsystem 20 and/or the dimension of the object, which is determined in the first subsystem 20, and of data (ii) of the second subsystem with respect to the position of the second camera device 31 within the second subsystem 20. The arrow (iii) makes it clear that the control signals that are generated in turn control the operation of the second subsystem 30, for example, with regard to an adjustment of the camera position or carrying out of a parameter matching.

The control unit 40 (not shown in FIG. 10), in which the control signals (iii) are generated, may be connected to a first database 41 and/or a second database 42. In the first database, data (iv) of dimensions for specific object profiles are stored. In the second database 42, data (v) of quality attributes for predetermined object profiles are stored. The assignment of the data arrows (iv) and (v) to the arrow (iii) symbolizes that the control signals of the control unit 40 may also express a function of the data of the first or second database. In other words, the operation of the second subsystem 30 may be carried out with consideration of the data of the first database 40 and/or with consideration of the data of the second database 41.

Figure 11:
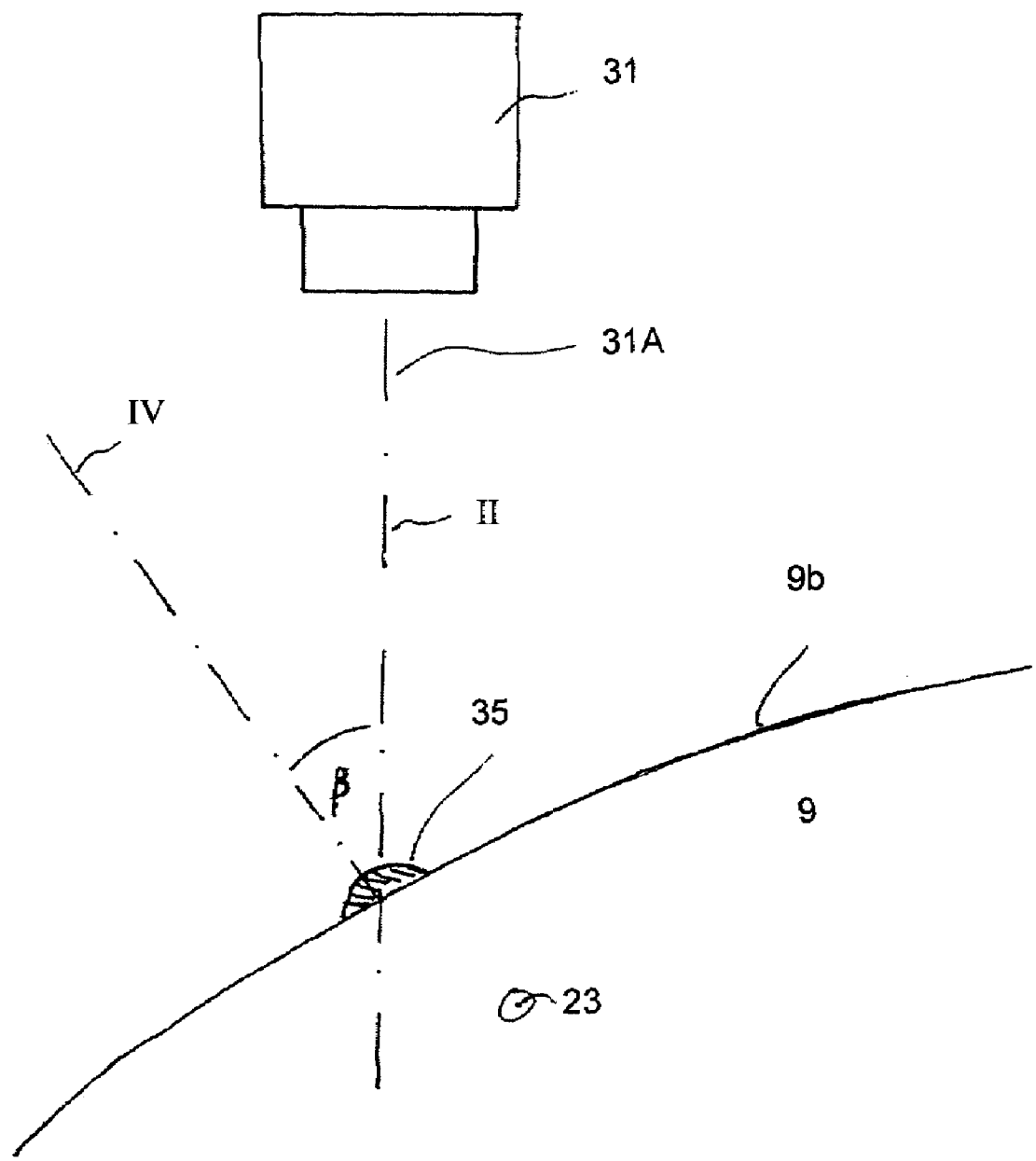
FIG. 11 shows in simplified form an angle transformation in the case of the second subsystem.

FIG. 11 shows the carrying out of the parameter adaptation referred to above, or an angle transformation. In FIG. 11, the second subsystem 30 is shown in a cross section, the axis 23 running perpendicularly to the plane of the drawing. Formed on the surface 9b of the object 9 is a defect in the form of an elevation 35, which is recorded by the electronic camera device 31. A possible parameter matching may in this case consist in an angle transformation with respect to the metered values of the surface structure of the object 9, on the basis of which a point of the surface 9b of the object recorded by the camera device is transformed in such a way that the recording axis 31A of the camera device lies virtually in a plane IV which is perpendicular to the surface of the object at the recording point. In the case shown, the recording axis 31A forms an angle $\beta$ with the plane IV. As a result, an advantageous imaging correction of the surface structure of the object 9 is achieved, in the case shown of the elevation 35.

By way of addition to the embodiments explained above, it is also possible for a number of subsystems 20 to be arranged one behind the other, in order to carry out the dimensional determination of the object 9 even more accurately. Furthermore, it is possible in the case of the second subsystem 30 for a plurality of the second electronic camera devices 31 to be arranged in a manually or automatically adjustable manner in the housing 26. Apart from a positional determination of these camera devices by means of the pointer elements 34, it is also possible to provide in the housing 26 sensor devices which detect a position of the camera devices 31 and correspondingly output it to the control device 40.

It should be noted that the matter contained in the above description and/or shown in the accompanying drawings should be interpreted as illustrative and not in a limiting sense. For example, when words such as "parallel" and "perpendicular" are used, that these may also include, respectively, essentially or approximately parallel and perpendicular geometry. The following claims are intended to cover all generic and specific features described herein, as well as all the statements of the scope of the present system and method, which, as a matter of language, might be said to fall there between.

What is claimed is:

1. A system (1) for measuring an object (9) and for monitoring the surface of the object (9), comprising:
 at least a first subsystem for determining one or more dimensions of the object (9) and a position of the object within the first subsystem, the first subsystem including at least a recording device and a first light source (22, 24);
 at least a second subsystem (30) for determining a surface structure of the object (9), the second subsystem (30) comprising at least an electronic camera device (31) and a second light source (32); and
 a control unit (40) generating control signals (iii) for operation of the second subsystem (30) as a function of data (I) of the first subsystem (20) with respect to a position of the object in the first subsystem and/or the dimension of the object, and of data (ii) of the second subsystem (30) with respect to the position of the camera device (31) in the second subsystem.

2. The system (10) of claim 1, wherein the position of the camera device (31) in the second subsystem (30) is predetermined before the initial operation of the system.

3. The system (10) of claim 2, wherein an information about the position of the camera device (31) in the second subsystem (30) before the initial operation of the system is sent to the control unit (40).

4. The system (10) of claim 1 or claim 2, wherein the camera device (31) in the second subsystem is positionable by a sensor device.

5. The system (10) of claim 1, wherein the recording device of the first subsystem (20) is a line detector.

6. The system (1) of claim 1, wherein the recording device of the first subsystem (20) is an electronic camera device (21).

7. The system (10) of claim 6, wherein the electronic camera device (21) of the first subsystem (20) and the electronic camera device (31) of the second subsystem (30) is the same electronic camera device.

8. The system (1) of claim 1, wherein the recording device (21) of the first subsystem (20) and the camera device (31) of the second subsystem (30) are placed in a common housing such that their recording regions are adjacent each other.

9. The system (10) of claim 7, additionally comprising:
 a pointing element (34) attached to the camera device (31) of the second subsystem (30) and detectable dependent on a position of the camera of the recording device (21) of the first subsystem (20), so as to determine the position of the camera device (31) within the second subsystem.

10. The system (1) of claim 1, wherein the camera device (31) is fixedly arranged in the second subsystem (30).

11. The system (1) of claim 1, wherein the position of the camera device (31) in the second subsystem (30) relative to the object (9) is adjustable in response to a control signal of the control unit (40).

12. The system (10) as claimed in claim 10, wherein the position of the camera device (31) is manually or automatically adjustable by means of a motor.

13. The system (1) of claim 1, wherein during the operation of the second subsystem (30) a parameter adaptation is executed for the metered values of the surface structure of the object (9) in response to the data of the first subsystem (20).

14. The system (1) of claim 13, wherein during the operation of the second subsystem (30), an angle transformation is executed with respect to the metered values of the surface structure of the object (9) is carried out, whereupon a point of a surface of the object captured by the camera device is transformed such that the recording axis (31A) of the camera device lies virtually in a plane (IV) which is perpendicular to the surface of the object at the recording point.

15. The system (1) of claim 1, wherein the recording axis (23a) of the camera device (31) in the second subsystem forms an angle (a) with a plane the plane being perpendicular to an axis of movement (23) of the object.

16. The system (1) of claim 1, wherein the control unit (40) is coupled to a first database (41), in which data (iv) of dimensions for predetermined object profiles are stored, the first subsystem (20) configured for detecting a predetermined object profile and the control signals (iii) of the control unit (40) being a function of the data (iv) of the first database (41).

17. The system (1) of claim 1, wherein the control unit (40) is coupled to a second database (42), in which data (v) of quality attributes for predetermined object profiles are stored, the control signals (iii) of the control unit being a function of the data (v) of the second database (42).

18. The system (1) of claim 17, wherein the second subsystem is configured such that a range of metered values with respect to a surface of the object (9) is specified as a function of the data stored in the first or second database.

19. The system (1) of claim 18, wherein the range of metered values is specified manually and/or automatically.

20. The system (1) of claim 1, wherein the first light source includes a laser (22) or an LED array (24), which emits radiation towards the object past a light blocking element (28) onto the surface of the object, in order to form a light edge (9a) on the object.

21. The system (1) of claim 1, comprising a plurality of first subsystems (20) and/or a plurality of second subsystems (30) and/or a plurality of control units (40).

22. A method for the quality inspection of an object (9), comprising the steps of:
 determining of one or more dimensions of the object (9) by means of a first subsystem (20), which comprises at least one recording device (21) and a first light source (22, 24);
 determining a surface structure of the object by means of a second subsystem (30), which comprises at least one electronic camera device (31) and a second light source (32); and
 generating of control signals (iii) for operation of the second subsystem (30) as a function of data (i) of the first subsystem with respect to a position of the object in the first subsystem and/or the dimension of the object, and of data (ii) of the second subsystem with respect to the position of the camera device in the second subsystem.

23. The method of claim 22, wherein the position of the camera device (31) in the second subsystem (30) is determined by a sensor device.

24. The method of claim 22, wherein the position of the camera device (31) inside the second subsystem (30) relative to the object (9) is adjusted in response to the control signals (iii).

25. The method of claim 22, wherein during an operation of the second subsystem a parameter adaptation with respect to the metered values of the surface structure of the object (9) is carried out in response to the data (i) of the first subsystem.

26. The method of claim 25, wherein during the operation of the second subsystem (30) an angle transformation with respect to the metered values of the surface structure of the object (9) is carried out, whereupon a point of a surface of the object captured and recorded by the camera device is transformed such that the recording axis (31 A) of the camera device lies virtually in a plane (IV) being perpendicular to the surface of the object at the recording point.

27. The method of claim 22, wherein the control signals (iii) are formed as a function of data of a first database (41), in which data (iv) include dimensions for predetermined object profiles, and the first subsystem (20) detects a predetermined object profile.

28. The method of claim 22, wherein the control signals (iii) are formed as a function of data of a second database (42), in which data (v) are quality attributes for predetermined object profiles.

29. The method of claim 22, wherein a range of metered values of the second subsystem with respect to a surface of the object is specified manually.

30. The method of claim 22, wherein a range of metered values of the second subsystem with respect to a surface of the object is specified as a function of the data stored in the first or second database.

31. The method of claim 30, wherein the range of metered values is specified manually and/or automatically.

32. The method of claim 22, wherein at least part of the steps is executable as a computer program with computer program means on a computer or a similar processing unit.

33. A computer program, comprising program coding means according to the method as claimed in claim 22, which program coding means are stored on a computer-readable data carrier.

34. A computer program product, comprising program coding means being stored on a computer-readable data carrier, to carry out the method as claimed in claim 22 when the computer program product is executed on a computer or on a similar processing unit.

35. A system (1) for measuring an object (9) and for monitoring the surface of the object (9), comprising:

at least a first subsystem for determining one or more dimensions of the object (9) and a position of the object within the first subsystem, the first subsystem including at least a recording device and a first light source (22, 24);

at least a second subsystem (30) for determining a surface structure of the object (9), the second subsystem (30) comprising at least an electronic camera device (31) and a second light source (32), and wherein during the operation of the second subsystem (30) a parameter adaptation is executed for metered values of the surface structure of the object (9) in response to the data of the first subsystem (20); and, a control unit (40) generating control signals (iii) for operation of the second subsystem (30) as a function of data (i) of the first subsystem (20) with respect to a position of the object in the first subsystem and/or the dimension of the object, and of data (ii) of the second subsystem (30) with respect to the position of the camera device (31) in the second subsystem.

36. A method for the quality inspection of an object (9), comprising the steps of:

determining of one or more dimensions of the object (9) by means of a first subsystem (20), which comprises at least one recording device (21) and a first light source (22, 24);

determining a surface structure of the object by means of a second subsystem (30), which comprises at least one electronic camera device (31) and a second light source (32);

generating of control signals (iii) for operation of the second subsystem (30) as a function of data (i) of the first subsystem with respect to a position of the object in the first subsystem and/or the dimension of the object, and of data (ii) of the second subsystem with respect to the position of the camera device in the second subsystem; and in response to the data (i) of the first subsystem, performing a parameter adaptation with respect to metered values of the surface structure of the object (9) during an operation of the second subsystem.

* * * * *